United States Patent [19]

De La Hoz

[11] Patent Number: 4,638,824
[45] Date of Patent: Jan. 27, 1987

[54] DENTAL FLOSS DEVICE

[76] Inventor: Jorge W. De La Hoz, 330 W. 10th St., Apt. #3, Hialeah, Fla. 33010

[21] Appl. No.: 773,869

[22] Filed: Sep. 9, 1985

[51] Int. Cl.⁴ .............................................. A61C 15/00
[52] U.S. Cl. ........................................ 132/91; 132/89
[58] Field of Search ................... 132/91, 89, 90, 92 R, 132/92 A, 93

[56] References Cited
U.S. PATENT DOCUMENTS 3,901,251 8/1975 Johnston ................................. 132/91
4,034,770 7/1977 Trecker .................................. 132/90
4,050,470 9/1977 Miller .................................... 132/89

Primary Examiner—John J. Wilson
Attorney, Agent, or Firm—Jesus Sanchelima

[57] ABSTRACT

This invention provides for devices to hold dental floss on the fingers to eliminate the need for wrapping the floss on the finger in order to use the floss. It has a substantially flat structure with a hole in it into which the finger on a user is inserted. It also has at least one prong for releasably affixing the floss to.

4 Claims, 4 Drawing Figures

DENTAL FLOSS DEVICE

BACKGROUND OF THE INVENTION

1. Field of the Invention

The present device relates to the area of dental hygiene products and more particularly to dental floss holders for use in cleaning between teeth with dental floss or thread.

2. Description of the Prior Art

In dental hygiene many products have been developed to promote gum and tooth health, many of which have been directed to the removal of the material buildup caused by bacteria in the mouth. One of the most widely accepted ways to remove material from between the teeth and stimulate the gums at such locations has been to run a thread between each pair of adjacent teeth, moving it back and forth to remove material found there and to simultaneously provide contact stimulation of the gums at those locations. Toothpicks have also been widely used but most do not provide the same access to the areas between closely spaced teeth that thread can. The development of properly strengthened thread has led to a variety of the so called "dental flosses" including wintergreen flavored or waxed threads which make the task of "flossing" easier or more pleasant.

In use of dental floss, the floss must be kept taut to be effective. Others have invented various devices which hold the floss tightly but commonly the fingers are used as posts upon which the floss is wound in various ways. Most often the user will pull the "posts" apart once he has the floss properly located between the teeth to produce this taughtness. The user may then work the floss between the teeth to produce the desired cleaning and stimulating effect.

This invention provides a device which does *not* require the user to wrap floss about his fingers and bind them (to make "posts") while at the same time it provides the user with the ability to make the floss taut for cleaning/stimulating between his teeth. It also provides the user with the ability to pull a length of floss completely through the space between two very tightly adjacent teeth. This can be essential where, in the lower jaw for instance, there is a problem in pulling the floss "up" from between two such teeth, or where there is some other impediment to "upward" removal. This invention also allows varying lengths of floss to be used.

Other patents describing the closest subject matter provide for a number of more or less complicated features that fail to solve the problem in an efficient and economical way. None of these patents suggest the novel features of the present invention.

SUMMARY OF THE INVENTION

This invention provides a device which is capable of holding a short length of floss taut between two teeth for cleaning or stimulation, while at the same time allowing for easy disengagement of the floss from either side of the floss length. It is inexpensive and easy to manufacture.

It is basically a pair of rings with floss holders formed on them from which the floss cannot slip when properly engaged.

Accordingly the primary object of this invention is to provide an easier and safer way to floss teeth.

Another object is to provide for an inexpensive apparatus which thus improves the users flossing.

Another object is to provide such an apparatus which requires only a small length of floss.

Further objects of the invention will be brought out in the following part of the specification, wherein detailed description is for the purpose of fully disclosing the invention without placing limitations thereon.

BRIEF DESCRIPTION OF THE DRAWINGS

With the above and other related objects in view, the invention consists in the details of construction and combination of parts as will be more fully understood from the following description, when read in conjunction with the accompanying drawings in which.

DETAILED DESCRIPTION OF THE PREFERRED EMBODIMENT

Figure 1:
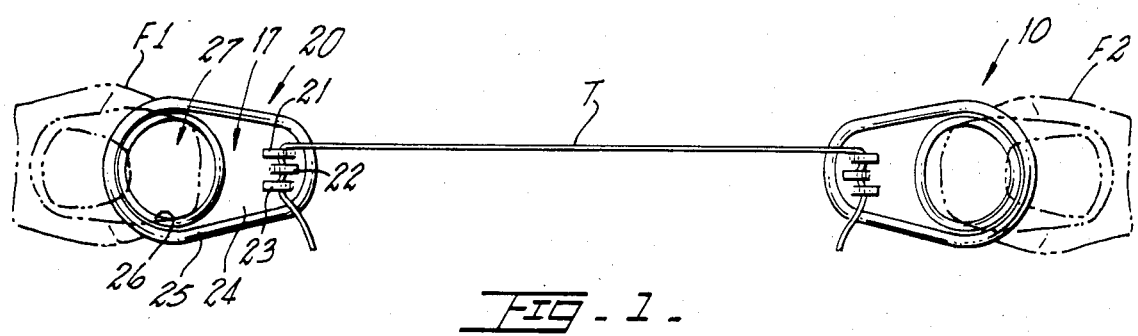
FIG. 1 depicts the preferred embodiment in use holding a thread or floss, "T", with tension.

Referring now to FIG. 1, the inventions preferred embodiment is depicted as a pair of rings 10 and 20, shown holding floss T tautly by the force of the user's fingers F1 and F2. (A single ring could of course be used upon one finger with the user holding the opposite end of the floss by some other means, but generally it is expected that two rings will be employed.)

The rings may be identical or mirror image. The ring 20, is held by the insertion of the finger F through aperture 27. For comfort, a rounded edge is provided, in the preferred embodiment by lip 26. Lip 27 also provides comfort and safety to the user where the ring 20 is inserted into the user's mouth.

Figure 4:
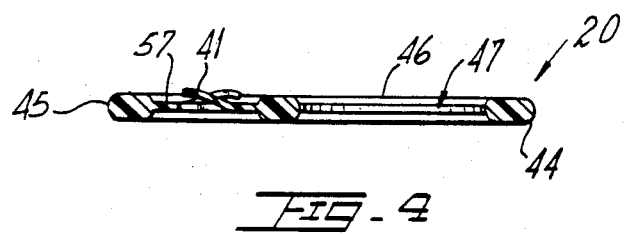
FIG. 4 depicts an alternative preferred embodiment, from the same view as FIG. 3 is of the first described preferred embodiment.

The entire ring is preferably formed of a sheet of metal but any suitable material will do, or various metal alloys or even a suitably hard plastic or polymer material. Aluminum is this inventors choice of metals because of the ease with which it may be stamped into the appropriate shape, its durability and its low price. A second preferred embodiment in which plastic is preferred to metal is shown in FIG. 4. Any material which will maintain the appropriate shape to function as described will suffice for the purposes of this invention. The choice of material used as a substrate may be dictated by the whim of the purchasing user or by the dictates of economy.

To removably connect the floss to the ring 20, three prongs 21, 22 and 23 are provided around which the floss T may be easily fastened and held in the manner illustrated in FIG. 1. While a single prong on which the floss may be caught may be sufficient to hold the floss fast to the ring, and because it may be more quickly threaded it may be preferred by some, the inventor herein prefers the three prongs provided as shown, at an angle from the plane of the deck, for the surest grip.

Figure 2:
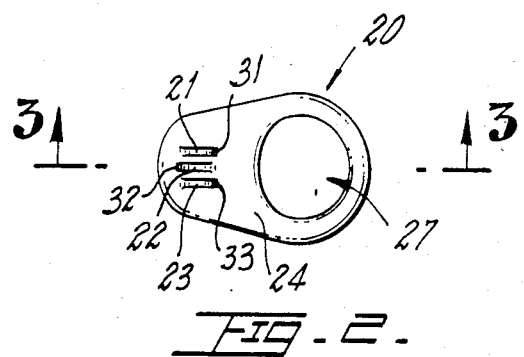
FIG. 2 is a front view of the obverse side of ring 20.
Figure 3:
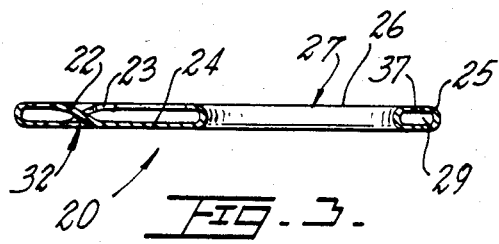
FIG. 3 is a cross sectional view of FIG. 2, taken at line 3—3 of FIG. 2.

Reference to FIGS. 2 and 3 show the detail of construction not seen in FIG. 1, said prongs 21, 22 and 23 being most easily fashioned as cut-out parts of the substantially flat substrate material 24 leaving spaces 31, 32 and 33 respectively.

In FIG. 3, lip 26 is shown to form a tube 29 with lip 25 which may or may not be open at 37 as long as a rounded edge is provided for the user's comfort.

It is important that the cut out prongs (for example prong 22 in FIG. 3) do not extend beyond nor above the surface (25s). This is to prevent the risk of injury to the user, especially when the prongs may be in the user's mouth. Access to the prong is provided by making the deck 17 (FIG. 1) large enough to easily position floss T onto it for fastening on the prong or prongs.

FIG. 4 pictures an alternative embodiment made of a substrate 44 in a shape more readily constructed of plastic than of metal. The tip of prong 41 may thus be less prone to cause injury and may be raised higher by something like the raised deck 57. Lip 46 in this embodiment forms a solid toroid shape around aperture 47. Prong 41 may be formed directly from lip 45.

It is believed the foregoing description conveys the best understanding of the objects and advantages of the present invention. Different embodiments may be made of the inventive concept of this invention. It is to be understood that all matter disclosed herein is to be interpreted merely as illustrative, and not in a limiting sense, except as set forth in the following appended claims.

What is claimed is:

1. A device for releasably holding dental floss in operative taughtness comprising:
    A. a substantially flat substrate containing an aperture so arranged, sized and disposed to admit the passage thereinto of a human finger at an angle substantially normal to the plane of said substrate;
    B. a lip, formed integrally with said aperture so as to remove any sharp internal edge from said aperture;
    C. a deck formed on said substrate wherein said deck includes three prong means and said flat substrate has substantially a toroidal shape, and said prong means protruding therefrom for releasably holding said dental floss.

2. A device as set forth in claim 1 further comprising a second lip formed integrally with said deck.

3. A device as set forth in claim 2 wherein said device is composed of aluminum.

4. A device as set forth in claim 3 wherein said device is composed of plastic.

* * * * *